United States Patent [19]

Batz et al.

[11] 4,202,873
[45] May 13, 1980

[54] ALKYLOLAMIDES OF IODIZABLE AMINO ACIDS AND IMMUNE TEST REAGENTS CONTAINING THEM

[75] Inventors: Hans-Georg Batz, Tutzing; Klaus Stellner, Bernried; Hans-Ralf Linke, Wielenbach; Günter Weimann, Tutzing, all of Fed. Rep. of Germany

[73] Assignee: Boehringer Mannheim GmbH, Mannheim-Waldhof, Fed. Rep. of Germany

[21] Appl. No.: 782,868

[22] Filed: Mar. 30, 1977

[30] Foreign Application Priority Data

Apr. 15, 1976 [DE] Fed. Rep. of Germany ....... 2616724

[51] Int. Cl.² .................. C07C 103/78; C07D 233/02; A61K 43/00
[52] U.S. Cl. ................................. 424/1; 260/559 A; 548/344
[58] Field of Search ....................... 260/559 A, 561 A; 424/1, 324

[56] References Cited

U.S. PATENT DOCUMENTS

| | | | |
|---|---|---|---|
| 3,189,646 | 6/1965 | Rainer | 260/561 A |
| 3,714,249 | 1/1973 | Norton | 260/559 A X |
| 3,763,234 | 10/1973 | Brill | 260/561 A X |

OTHER PUBLICATIONS

Chem. Abs., vol. 77, 1972, 118,873g, "Protection of Some Peptides and Aminoacids by Tritylation", Halstrom, S. et al.

Chem. Abs., vol. 79, 1973, 65,257q, "Protection of N-H Bonds & Tertiary Amino Groups", Barton, J.

Primary Examiner—Allen B. Curtis
Attorney, Agent, or Firm—Sprung, Felfe, Horn, Lynch & Kramer

[57] ABSTRACT

Novel alkylolamides of iodizable amino acids of the formula

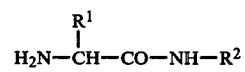

wherein,
$R^1$ is hydroxybenzyl, dihydroxybenzyl or imidazol-4-yl-methyl and
$R^2$ is monohydroxy-alkyl of 1 or 2 carbon atoms or dihydroxy-alkyl of up to 4 carbon atoms, and the water-soluble salts thereof are provided; these materials are useful as components of radioiodizable immune test reagents.

8 Claims, No Drawings

ALKYLOLAMIDES OF IODIZABLE AMINO ACIDS AND IMMUNE TEST REAGENTS CONTAINING THEM

The present invention is concerned with alkylolamides of iodizable amino acids and with the preparation thereof. Such compounds are useful in the preparation of immune test reagents, and the invention thus relates, in further aspect, to such reagents.

For the preparation of reagents which are employed in immunological tests in aqueous or physiological solution, for example in plasma, serum or urine, use is frequently made of substances which are radiomarkable, substances which are radioiodizable with the iodine isotopes $^{125}I$ and $^{131}I$ being preferred. Since the iodine isotopes can only seldom be introduced directly into the molecule to be investigated or determined without irreversibly changing or inactivating this molecule, in general, easily iodizable substances, for example the amino acids tyrosine, dihydroxyphenylalanine, 5-hydroxytryptophane or histidine or derivatives thereof, such as esters, biogenic amines or hydroxy derivatives, are coupled on to the substance to be investigated.

Thus, an immune test is known for the determination of digitoxin and digoxin in which, as radioiodizable substance, there is used a tyrosine methyl ester-containing compound (see, for example, J. Clin. Investig., 47, 1035–1042).

Furthermore, German Patent Specification No. 2,142,421 describes conjugates of digitoxigenin derivatives and tyrosine, i.e. conjugates with a free carboxyl group.

However, these known conjugates suffer from various disadvantages. Thus, the coupling products with the amino acid esters or the biogenic amines are strongly hydrophobic and either have a low water-solubility or are water-insoluble. The conjugates with free amino acids, on the other hand, suffer from the disadvantage that they are difficult to synthesize and the yields obtained are poor because the solubility of amino acids in organic solvents is too low and, furthermore, the selective hydrolysis of amino acid lower alkyl esters, besides a further ester group in the molecule, are difficult to carry out. In addition, a free carboxyl function can lead to undesired side reactions with the sample serum to be investigated and thus, under certain circumstances, can impair the test.

The present invention avoids these disadvantages and to provide hydrophilic, non-polar, iodizable amino acid derivatives which are readily soluble in water and physiological fluids and which can be prepared in improved yields and thus more economically and are suitable for the preparation of immune test reagents.

The present invention provides novel alkylolamides of iodizable amino acids of the formula:

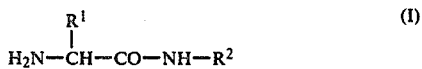
(I)

wherein $R^1$ is a hydroxybenzyl, dihydroxybenzyl or imidazol-4-yl-methyl radical and $R^2$ is a monohydroxyalkyl radical containing 1 or 2 carbon atoms or a dihydroxyalkyl radical containing up to 4 carbon atoms, as well as the water-soluble salts thereof.

The hydroxybenzyl radical is preferably the p-hydroxybenzyl radical and the dihydroxybenzyl radical is preferably the 3,4-dihydroxybenzyl radical. Examples of monohydroxyalkyl radicals containing 1 or 2 carbon atoms and of dihydroxyalkyl radicals containing up to 4 carbon atoms include the methylol, ethylol, 1,3-dihydroxypropyl, 1,4-dihydroxybutyl and dihydroxy-tert.-butyl radicals. Examples of water-soluble salts include the salts of all mineral acids, the easily crystallisable hydrohalides being preferred.

Especially preferred alkylolamides according to the present invention include tyrosylethanolamide hydrochloride and histidylethanolamide hydrochloride.

The compounds according to the present invention are hydrophilic and are easily soluble in water and physiological fluids and, because of their reactive amino group, can be easily conjugated to iodisable tracer substances and can be especially easily coupled with acid derivatives with the formation of an amide bond and thus are especially suitable for the preparation of reagents for immunological tests in aqueous and physiological solution.

The use of compounds according to the present invention is especially advantageous for the preparation of reagents for the investigation of cardiac glycosides (Digitalis glycosides). For this purpose, the alkylolamides according to the present invention can be reacted with digoxin, digoxigenin, digitoxin or digitoxigenin derivatives, for example with the digoxin or digitoxin dicarboxylic acid esters in the manner described in German Patent Specification No. 2,537,129. When using the compounds according to the present invention for the preparation of such reagents, no undesired side reactions occur, for example, with the sample serum in the case of a radioimmune test because, inter alia, the alkylolamides according to the present invention do not contain a free carboxyl group in the molecule.

The alkylolamides of iodisable amino acids according to the present invention can be prepared by first protecting, with a protective group, the amino group of the amino acid upon which the alkylolamide is based, then esterifying the carboxyl group of the amino acid with a reactive compound which can be split off aminolytically, reacting the ester so obtained with an alkanolamine containing 1 or 2 carbon atoms or with an alkanediolamine containing up to 4 carbon atoms to give the corresponding amide, splitting off the protective group in an acidic medium or reductively and, if desired, converting the amino acid alkylolamide thus obtained into a water-soluble salt by acidification.

According to the process of the present invention, the protective group can be, for example, a trifluoroacetyl, carbobenzoxy or trityl group and the reactive compound which can be split off aminolytically can be, for example, the hydroxyacetonitrile, hydroxysuccinimide or N-hydroxybenztriazole esters which can be prepared, for example, from the acids and the hydroxy compounds or from the alkali metal salts of the acids and, for example, chloroacetonitrile, hydroxysuccinimide sulphonate, N-hydroxybenztriazole tosylate, N-hydroxybenztriazole trifluoromethyl sulphonate or 2,4,5-trichlorophenyl sulphonate.

The following Examples are given for the purpose of illustrating the present invention:

EXAMPLE 1

Tyrosylethanolamide hydrochloride (a) According to the procedure described by F. Weygand and R. Geiger (Chem. Ber. 89, 647/1956), N-trifluoroacetyltyrosine was prepared by the reaction of tyrosine with trifluoroacetic anhydride in a mixture of trifluoroacetic acid and diethyl ether.

(b) To a solution of 10 g. (36 mMol) trifluoroacetyltyrosine and 4.6 g. (40 mMol) N-hydroxysuccinimide in anhydrous tetrahydrofuran, there was added dropwise, with stirring and ice cooling, a solution of 8.5 g. (41.2 mMol) dicyclohexyl carbodiimide in anhydrous tetrahydrofuran. The reaction mixture was subsequently stirred for 12 hours at ambient temperature, precipitated dicyclohexyl-urea was then filtered off and the filtrate was evaporated and the residue taken up in ethyl acetate. The ethyl acetate solution was shaken out with water, aqueous sodium bicarbonate solution and again with water, dried over anhydrous sodium sulphate and evaporated. The precipitated N-trifluoroacetyl-tyrosyl-hydroxysuccinimide ester was recrystallised from petroleum ether. Yield: 11.3 g. (84% of theory); m.p. 145°–147° C.

Analysis: $C_{15}H_{13}O_6N_2F_3$ (374.27): Calculated: C 48.14%; H 3.50%; N 7.48 Found: C 48.68%; H 3.23%; N 7.28

(c) 7.6 g. (20.3 mMol) N-trifluoroacetyl-tyrosyl-hydroxysuccinimide ester were dissolved in 60 ml. dioxan and mixed with a solution of 2.1 g. (34.4 mMol) ethanolamine in water. The solution was then adjusted to pH 7.5 with a 5% aqueous solution of potassium carbonate and stirred for four days at ambient temperature. Subsequently, the solution was evaporated and the residue was taken up in methanol and fractionated over a silica gel column (elution agent: methanol/chloroform mixture 1:1). The uniform product fractions were evaporated and recrystallised from ether. Yield: 3.9 g. (45% of theory) N-trifluoroacetyl-tyrosyl-ethanolamide; m.p. 153°–155° C.

Analysis: $C_{13}H_{15}O_4N_2F_3$ (320.27): Calculated: C 48.75%; H 4.72%; N 8.74 Found: C 47.91%; H 4.07%; N 8.40

(d) 4.3 g. (13.4 mMol) N-trifluoroacetyl-tyrosyl-ethanolamide were dissolved in 30 ml. absolute ethanol and mixed with 2 g. (53 mMol) sodium borohydride and the reaction mixture stirred for 1 hour. It was then mixed with 30 ml. acetone and further stirred for 30 minutes. The reaction mixture was then evaporated and the residue was taken up in water and shaken out with a little ethyl acetate. The aqueous solution was evaporated to dryness and the residue was taken up in a mixture of ethanol and chloroform, filtered and concentrated. The residue was taken up in ethanol and hydrogen chloride was then passed into this solution, the hydrochloride of tyrosylethanolamide thereby precipitating out. Yield: 2.5 g. (70% of theory); m.p. 220°–225° C. (decomp.).

EXAMPLE 2

Histidylethanolamide hydrochloride (a) According to the original literature procedure of A. Patchornik et al. (J.A.C.S., 79, 6416/1957), 1,N-dicarbobenzoxy-L-histidine was prepared by the reaction of L-histidine with carbobenzoxy chloride.

(b) 1,N-Dicarbobenzoxy-L-histidine-hydroxysuccinimide ester was prepared analogously to Example 1 (b).

Reaction mixture:
1,N-dicarbobenzoxy-L-histidine: 27.5 mM = 12.5 g.
N-hydroxysuccinimide: 30.0 mM = 3.5 g.
dicyclohexyl carbodiimide: 30.0 mM = 6.2 g.

Yield: 10.2 g. (71% of theory); melting point: 135°–138° C. (decomposition)
Analysis: $C_{26}H_{24}N_4O_8$ (520.51): Calculated: C 60.0%; H 4.61%; N 10.76 Found: C 60.44%; H 4.55%; N 10.54

(c) 9.8 g. (18.7 mMol) 1,N-dicarbobenzoxy-L-histidine-hydroxysuccinimide ester were dissolved in 80 ml. dioxan and mixed with a solution of 5.45 g. (56.0 mM) ethanolamine in water. The solution was then adjusted to pH 7.5 with a 5% aqueous solution of potassium carbonate and stirred for 24 hours at ambient temperature. Subsequently, the solution was evaporated and the residue was taken up in water and shaken out twice with chloroform. The aqueous solution was evaporated and the oily residue dried.

The oil so obtained was mixed, while stirring, with 20 ml. 40% hydrobromic acid in anhydrous glacial acetic acid and stirred for half an hour at ambient temperature. The solution was mixed with 100 ml. anhydrous diethyl ether, an oil thereby separating out which was dissolved in a little water and adjusted to pH 8.0 with a 5% aqueous solution of potassium carbonate.

The solution was evaporated and the residue was taken up in anhydrous methanol, filtered off from separated salt and the filtrate evaporated.

The residue was dried under oil pump vacuum and subsequently taken up in absolute ethanol. Hydrogen chloride was then passed into the solution, the hydrochloride of histidylethanolamide thereby precipitating out.

Yield: 2.9 g. (51% of theory); Melting point: 290°–300° C. (decomp.).

Use of the compound according to Example 1 for the preparation of a radioiodisable reagent for the investigation of cardiac glycosides.

Preparation of digoxin-4'''-glutaryl-tyrosyl-ethanolamide.

200 mg. digoxin-4'''-glutaryl-hydroxysuccinimide ester, prepared according to Example 4 of German Patent Specification No. 2,537,129, were dissolved in 20 ml. absolute ethanol and mixed with 60 mg. of the tyrosyl-ethanolamide hydrochloride prepared according to Example 1 in 5 ml. water. The solution was then adjusted to pH 8.0 with a 5% aqueous solution of potassium carbonate and stirred for 3 days at ambient temperature. The solution was then evaporated and the residue was taken up in absolute ethanol, filtered and dried. For purification, the product was taken up in a mixture of ethanol and ethyl acetate and chromatographed over a silica gel column. Impurities were eluted with ethyl acetate and the pure product with ethanol. Yield: 135 mg. (63% of theory).

Analysis: $C_{57}H_{85}N_2O_{19}$ (1101): Calculated: C 62.1%; H 7.7%; N 2.5% Found: C 60.84%; H 7.78%; N 2.21%

The digoxin-4'''-glutaryl-tyrosyl-ethanolamide so prepared is, after radioactive marking with $^{125}I$, an excellent non-polar reagent for the determination of digoxin in aqueous or physiological solution.

It will be understood that the specification and examples are illustrative but not limitative of the present invention and that other embodiments within the spirit and scope of the invention will suggest themselves to those skilled in the art.

What is claimed is:
1. Alkylolamide of an iodizable amino acid, of the formula:

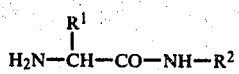

wherein,
R¹ is hydroxybenzyl or dihydroxybenzyl and
R² is monohydroxyl-alkyl of 1 or 2 carbon atoms or dihydroxyalkyl of up to 4 carbon atoms,
and the water-soluble salts thereof.

2. Alkylolamide as claimed in claim 1 wherein R¹ is hydroxybenzyl.

3. Alkylolamide as claimed in claim 1 wherein R¹ is dihydroxybenzyl.

4. Alkylolamide as claimed in claim 1 wherein R² is monohydroxy-alkyl of 1 or 2 carbon atoms.

5. Alkylolamide as claimed in claim 1 wherein R² is dihydroxy-alkyl of up to 4 carbon atoms.

6. Alkylolamide as claimed in claim 1, designated tyrosylethanolamide hydrochloride.

7. Radioiodizable reagents for immune tests in aqueous or physiological solution comprising an alkylolamide of an iodizable amino acid as claimed in claim 1.

8. Radioiodized reagents for immune tests in aqueous or physiological solution, comprising a radioiodized alkylolamide of an iodizable amino acid as claimed in claim 1.

* * * * *